United States Patent [19]
Badolato et al.

[11] Patent Number: 4,668,394
[45] Date of Patent: May 26, 1987

[54] FILTRATION MEDIA AND SUPPORTING FRAME

[75] Inventors: Anthony Badolato, Willingboro, N.J.; Melissa A. Prince, San Francisco, (San Francisco County), Calif.

[73] Assignee: McNeilab, Inc., Fort Washington, Pa.

[21] Appl. No.: 456,649

[22] Filed: Jan. 10, 1983

[51] Int. Cl.⁴ ............................................. B01D 29/14
[52] U.S. Cl. ..................................... 210/314; 210/317; 210/484; 210/489; 210/495; 55/483; 55/501; 55/DIG. 31; 604/5
[58] Field of Search ............ 210/927, 491, 508, 195.1, 210/253, 257.1, 295, 314, 317, 323.1, 335, 484, 488, 489, 490, 495, 485, 335, 315; 55/DIG. 31, 501, 503, 518, 483, 529, 482, 485, 486; 604/4–6

[56] References Cited

U.S. PATENT DOCUMENTS

| | | | |
|---|---|---|---|
| 3,003,643 | 10/1961 | Thomas | 210/491 |
| 3,450,632 | 6/1969 | Olson et al. | 210/508 |
| 3,511,382 | 5/1970 | Mesek | 210/491 |
| 3,593,854 | 7/1971 | Swank | 210/491 |
| 3,659,719 | 5/1972 | Westlin et al. | 55/DIG. 31 |
| 3,717,256 | 2/1973 | Parrott et al. | 55/DIG. 31 |
| 3,950,157 | 4/1976 | Matney | 55/529 |
| 4,073,732 | 2/1978 | Lauer et al. | 210/491 |
| 4,115,277 | 9/1978 | Swank | 210/927 |
| 4,190,426 | 2/1980 | Ruschke | 210/927 |
| 4,330,410 | 5/1982 | Takenaka et al. | 210/927 |

FOREIGN PATENT DOCUMENTS

| | | | |
|---|---|---|---|
| 251936 | 5/1964 | Australia | 210/491 |
| 96163 | 7/1980 | Japan | 210/927 |

Primary Examiner—Benoit Castel
Assistant Examiner—Wanda L. Milland
Attorney, Agent or Firm—Laurence D. Schuler

[57] ABSTRACT

A filtration unit comprising a filtration media sub-unit secured in an outer frame. The sub-unit comprises a fibrous filtration media enclosed in an inner frame having an upstream frame element and a downstream frame element. Each frame element has longitudinal and transverse struts and the intersections of these struts are in a single plane on the side of the frame elements which contact the filtration media. In one embodiment the filtration unit is enclosed in a sock of knit fabric; in another embodiment, there is a piece of knit fabric between the outer frame and the downstream frame element of the inner frame. The longitudinal struts may have portions which are perpendicular to and project beyond the principal plane of the periphery of the downstream frame element. If such perpendicularly projecting portions are provided, they are preferably arcuate in configuration.

5 Claims, 2 Drawing Figures

FILTRATION MEDIA AND SUPPORTING FRAME

FIELD OF THE INVENTION

The present invention relates to filtration media for use in filtering liquids. More particularly, the invention relates to a filtration medium for filtering blood. The filtration media of the present invention is especially useful for filtering blood passing through a cardiotomy reservoir with filter.

BACKGROUND OF THE INVENTION

There are currently in use many medical procedures for the extracorporeal treatment of blood. Some of these procedures involve removal of blood from a patient, circulation of the removed blood through an extracorporeal blood circuit including a device for treating the blood, and return of the circulated, treated blood to the patient. Typical procedures of this type are blood dialysis, blood oxygenation, and hemoperfusion. Other treatment procedures involve the separation of the removed blood into one or more of its component parts, treatment of said one or more components in an extracorporeal environment, and return of the separated, treated component(s) to the patient. Illustrative of this type of procedure is one in which blood is separated into a plasma fraction and a cellular or "formed element" fraction, the plasma fraction is chilled and filtered, the filtered plasma fraction is warmed and recombined with the cellular fraction, and the recombined fractions are returned to the patient. This type of procedure is disclosed in U.S. Pat. No. 4,350,156.

The extracorporeal circuits used to carry out the aforementioned treatment procedures may require the use of a fluid reservoir as well as the specific device needed to effect the desired treatment. For example, in the case of open heart surgery, where either a bubble oxygenator or a membrane oxygenator is employed to take over the gas exchange function of the patient's lungs, a device known as a cardiotomy reservoir is generally included in the extracorporeal circuit to receive and hold banked blood and/or blood collected by the application of suction from the opened chest cavity of the patient ("cardiotomy blood"). Cardiotomy reservoirs usually include a defoamer for defoaming cardiotomy blood and banked blood and an internal chamber in which the defoamed blood may be temporarily stored to await further use at various stages of the surgical procedure. A cardiotomy reservoir has at least one and, usually, several inlet ports communicating with its interior. Where there are two or more inlets, one may be used for the addition of banked blood and another may be used for admission of cardiotomy blood. The cardiotomy reservoir further includes an outlet port through which blood is withdrawn to be conducted downstream thereof, usually to the blood inlet of the oxygenator.

In addition to a blood defoamer element, cardiotomy reservoirs frequently include a blood filtration media for filtering the blood after it has been defoamed, such devices being referred to as "cardiotomy reservoirs with filters." The purpose of filtering the blood after it has been defoamed is to remove undesirable particulate matter such as blood clots, aggregated blood cells, and debris from the site of surgery. As a practical matter, a blood filtration media should not be designed to remove undesirable particulate matter of less than about 20 microns in size. This is because the size of white blood cells typically is as high as about 18 microns and a filtration media capable of filtering particles of less than about 20 microns will not only remove the aforementioned undesirable particulate matter but may very likely also remove white blood cells or other desirable components of the blood. It is desirable therefore to provide a blood filtration media which is capable of efficiently removing particulate matter whose size is equal to or greater than 20 microns.

SUMMARY OF THE INVENTION

In accordance with the present invention, there is provided a filtration media whose mean efficiency, at the 95 percent confidence level, in removing particulate matter of a size equal to or greater than 20.2 microns lies in the interval between 92.6 percent and 93.6 percent. This filtration media comprises three layers of synthetic fibers which are non-harmful to blood. The upstream layer (i.e., the layer first contacted by blood to be filtered) and the first downstream layer comprising the filtration media are, within the ranges to be recited hereinafter, substantially identical to each other but are different from the second downstream layer. All three of the fibrous layers are preferably provided in the form of a needle-loomed, calendered nonwoven fabric but bonded nonwovens or mats of fibers may also be used. It is preferred that polyester fibers be used in all three layers, but other synthetic fibers such as nylon, or blends of nylon and polyester fibers, may be used.

The denier of the synthetic fibers comprising the upstream layer and the first downstream layer should range from 4–8. The thickness of these two layers may range from about 0.035 inch (0.09 cm.) to about 0.080 inch (0.203 cm.) and preferably ranges from about 0.040 inches (0.102 cm.) to about 0.060 inches (0.152 cm.). The two layers may have a weight of from about 6.5 ounces per square yard to about 11.5 ounces per square yard. The mean pore size of the first two layers may range from about 40–80 microns and preferably ranges from 50–70 microns. The bubble point (as determined by ASTM Test F 316–70[1976] using mineral oil as the test fluid) of the two layers must be a minimum of about 2.5 inches (6.35 cm.) of water.

The denier of the synthetic fibers comprising the second downstream layer of fibers should range from about 22–28. The thickness of this layer may range from about 0.030 inch (0.076 cm.) to about 0.070 inches (0.178 cm.) and preferably ranges from 0.040 inch (0.102 cm.) to 0.060 inch (0.152 cm.). The second downstream layer should weigh between about 6.5 ounces per square yard and about 11.0 ounces per square yard. The mean pore size of this layer may range from 35 to 60 microns and preferably ranges from 40 to 50 microns. Its bubble point (as determined by ASTM Test F 316–70[1976] using mineral oil as the test fluid) must be at least about 4.0 inches (10.16 cm.) of water.

In a preferred embodiment of the invention, the above described filtration media is enclosed in a sock of knit polyester tricot fabric. This fabric typically has a pore size ranging from 85 to 115 microns, a thickness of 0.25 mm ±0.01 mm, and a bubble point (as determined by ASTM Test F 316–70[1976] using mineral oil as the test fluid) of at least 2.0 inches (5.1 cm.) of water. The advantages of enclosing the filtration medium in a knit tricot sock are that additional blood defoaming is obtained and the possibility of fragments of fiber from the fibrous layers being entrained in the blood is greatly reduced.

In another aspect of the invention, the three-stage filtration media is placed in a first frame to provide a filtration media sub-unit. This sub-unit is then fitted into another frame to provide a filtration unit which is then placed inside the aforementioned tricot fabric sock to provide a blood filtration assembly. The latter assembly can be readily fitted into a blood filtration device such as a cardiotomy reservoir with filter. Other aspects of the present invention will become apparent hereinafter.

The invention will be illustrated and more clearly understood with reference to the appended drawing in which.

DETAILED DESCRIPTION OF THE INVENTION

Figure 1:
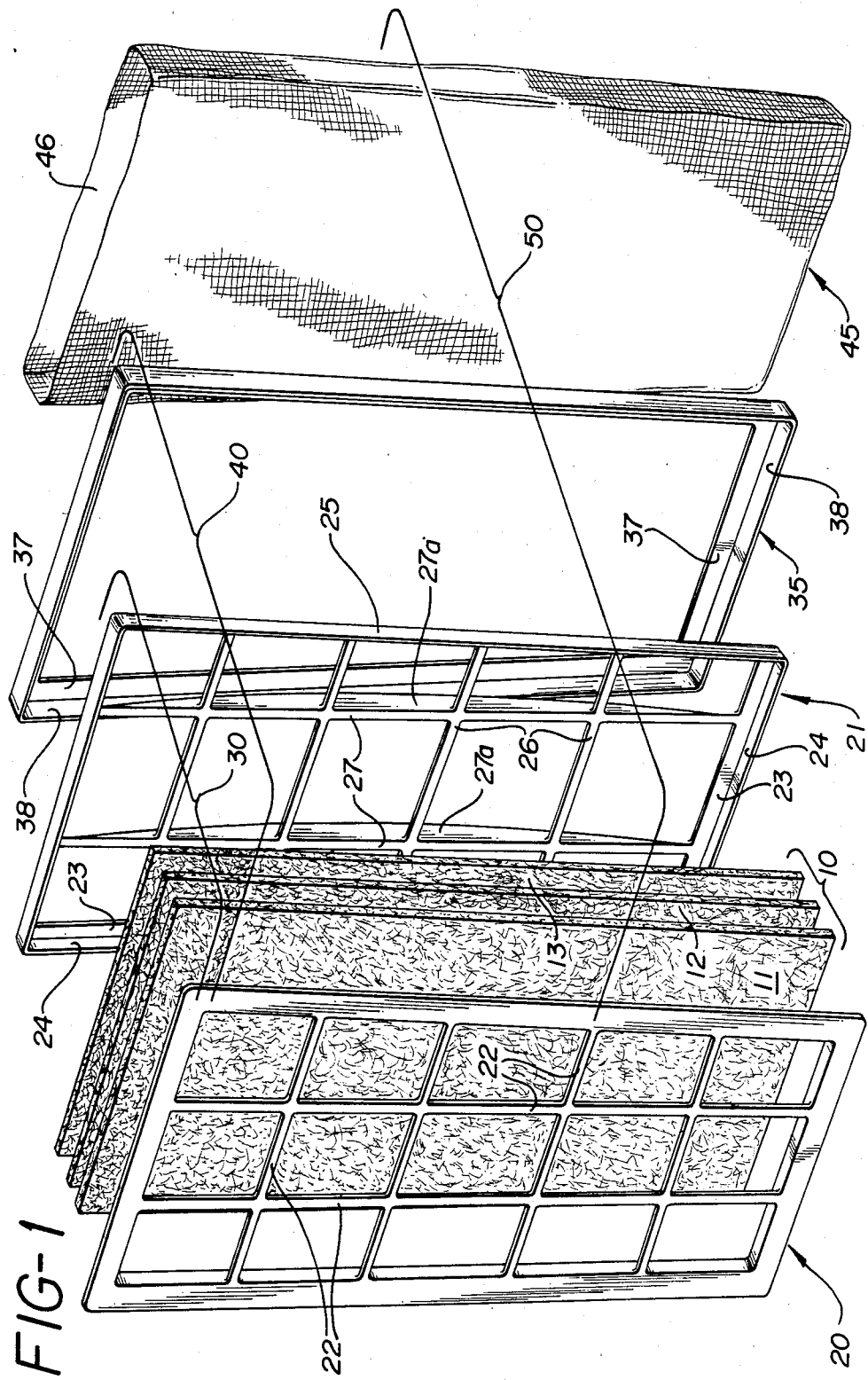
FIG. 1 is an exploded view showing the filtration media of the invention as well as the frames and sock which, together with the filtration medium, comprise the blood filtration assembly of the invention.

Referring now to FIG. 1 of the drawing, there is shown blood filtration media 10 comprising an upstream fibrous layer 11, a first downstream fibrous layer 12, and a second downstream fibrous layer 13. In use, blood to be filtered first passes through fibrous layer 11, then through fibrous layer 12, and thereafter through fibrous layer 13.

In a specific embodiment, upstream layer 11 and first downstream layer 12 were the same. Each of these layers comprised a needle-loomed, calendered polyester nonwoven fabric in which the denier of the polyester fibers was 6. The weight of the nonwoven fabric was about 8.9 ounces per square yard and its thickness was about 0.043 inch (0.109 cm.). The mean pore size of each fibrous layer was 64.3 microns. The bubble point of the fibrous layers, as determined by ASTM Test F 316-70(1976) using mineral oil as the test liquid, was 3.0 inches (7.62 cm.) of water.

In the specific embodiment under discussion, second downstream layer 13 also comprised a needle-loomed, calendered polyester nonwoven fabric. In this case, however, the denier of the polyester fibers was about 25. The weight of the fabric was about 10 ounces per square yard and its thickness was about 0.045 inch (0.114 cm.). Its bubble point, using the bubble point test method and test liquid described earlier, was 4.5 inches (11.4 cm.) of water. The pore size of this layer 13 was 46.3 microns.

Preferably, fibrous layers 11, 12 and 13 are needle-loomed, that is, the fibers comprising the layers are held together by mechanical engagement and entanglement of fibers. There is no reason, however, why the fibers in the fibrous layer cannot be unified by, e.g., solvent bonding, the application of a suitable adhesive, or the like.

As seen in the drawing, the three fibrous layers, which may be of any desired size or shape, are assembled in face-to-face relationship. The assembled fibrous layers are inserted in a frame comprising two mating frame members 20 and 21 to form a filtration media sub-unit 30. Frame member 20 comprises a U-shaped channel around the periphery of one of its major surfaces (specifically, the surface which is not seen in FIG. 1) and has transverse and longitudinal structural elements or struts 22. Two of the struts join the top and bottom edges of frame element 20, while two others join the side edges. The intersections of the struts are in a single plane so as to minimize bulk. The struts are of minimum width so as not to unduly reduce the filtration efficiency of the filtration media. The periphery of frame element 21 is generally L-shaped in cross-section, with the horizontal portion of the "L" forming a peripheral base 23 and the vertical portion of the "L" forming side walls 24. Frame element 21 further comprises transverse structural elements or struts 26 and longitudinal structural elements or struts 27. Struts 27 join the top and bottom edges of the frame and struts 26 join the side edges. The junctures of the transverse and longitudinal struts are in a single plane on the inner surface (the surface which contacts the filtration media) of frame element 21. As can be seen in the drawing, struts 27 have portions 27a, which are preferably arcuate in configuration, extending perpendicular to and beyond the principal plane of frame element 21.

Frame elements 20 and 21 are fitted to each other, with filtration medium 10 therebetween, by pressing edges 25 of side walls 24 into the U-shaped channel on the periphery of frame element 20 to form blood filtration sub-unit 30. The thickness of side wall 24 and the width of the aforementioned U-shaped channel are sized so as to provide a friction fit between frame elements 20 and 21. If desired, other suitable means may be used, alone or in conjunction with the friction fit, to retain the two frame elements in their assembled configuration. Struts 22, 26 and 27 have a dual function. First, they serve to increase the overall strength and stability of the two frame elements 20 and 21 and the blood filtration sub-unit 30. They also provide additional backing support for the blood filtration media which is enclosed between the frame elements. This minimizes undesirable bulging of the filtration media beyond the major surfaces of blood filtration sub-unit 30.

Blood filtration sub-unit 30 is assembled, e.g., with a friction fit, into frame 35 to form blood filtration unit 40. The structure of frame 35 is L-shaped in cross-section, having a peripheral base 37 formed by the horizontal portions of the "L" and side walls 38 formed by the vertical portions of the "L". Frame 35, which preferably consists only of its peripheral portions and has no reinforcing struts, provides further structural rigidity to unit 40.

In the preferred embodiment, filtration unit 40 is enclosed within a knit fabric sock 45, which is also made of polyester fiber. This sock is easily constructed by folding a suitably sized piece of knit polyester tricot fabric in half lengthwise and sewing, heat sealing or otherwise joining the bottom and side edges and leaving an open end 46. The sock is then turned inside out so the sewn or sealed edges are located interiorly. Filtration unit 40 is then placed inside the sock and open end 46 of the sock is closed over, again by heat sealing, sewing or the like, to give blood filtration assembly 50.

Figure 2:
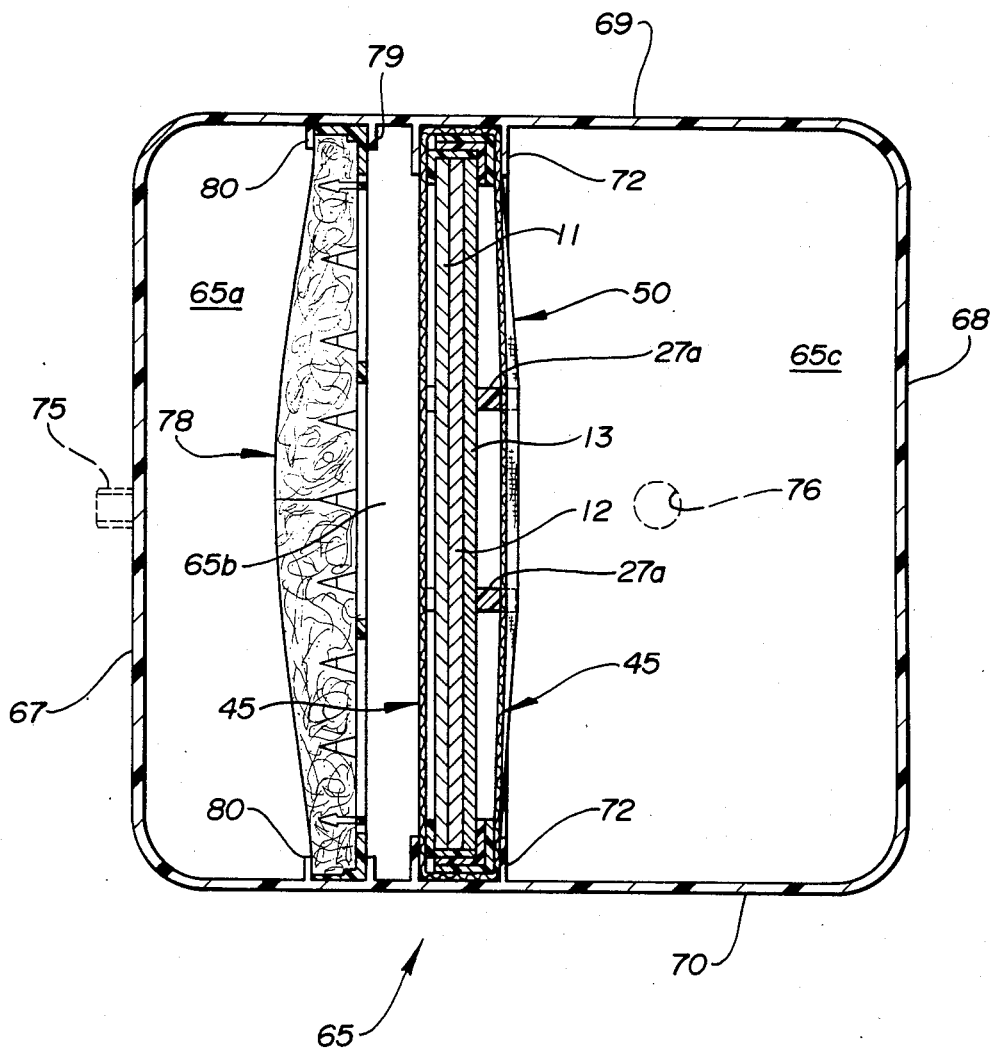
FIG. 2 is a transverse cross-section of a cardiotomy reservoir which includes the blood filtration media of the present invention.

FIG. 2 is a transverse cross-section of a cardiotomy reservoir comprising the blood filtration media of the present invention. Cardiotomy reservoir 65 includes a front wall 67, a back wall 68, two side walls 69 and 70, a blood inlet 75 located in front wall 67, a blood outlet 76 located in the bottom wall, a porous blood defoamer element 78 in a frame 79, and blood filtration assembly 50.

A suitable blood defoamer element 78 and frame 79 are more fully described in copending patent application Ser. No. 456,650, filed simultaneously with this application and entitled "Frame for Holding Defoamer Element or the Like." The blood defoamer/frame assembly is carried in a pair of U-shaped channels 80 integrally molded in side walls 69 and 70 of reservoir 65. Blood filtration assembly 50 is similarly carried in a pair of integrally-molded U-shaped channels 72. A blood receiving sub-chamber 65a is defined in cardiotomy reservoir 65 by front wall 67 and framed defoamer element 78. A second sub-chamber 65b for receiving defoamed blood is defined by framed defoamer element 78 and one major surface of blood filtration assembly 50. A third sub-chamber 65c for receiving defoamed, filtered blood is defined by the second major surface of blood filtration assembly 50 and back wall 68.

In use, blood from either a blood bank or the operative site, is admitted into sub-chamber 65a via blood inlet 75. This incoming blood is defoamed by the porous blood defoamer element 78. The defoamed blood passes into sub-chamber 65b, which preferably has a small cross-section so as to minimize the volume of blood therein, after which it passes through the blood filtration assembly. During such passage the blood is filtered by its passage through fibrous filtration layers 11, 12 and 13, and is also defoamed by the knit tricot sock. The defoamed, filtered blood is collected and temporarily retained in sub-chamber 65c until it is conducted downstream of the cardiotomy reservoir 65 via blood outlet 67.

A cardiotomy reservoir with which the blood filtration media of the present invention may be used is described in greater detail in copending patent application Ser. No. 456,651, filed simultaneously herewith and entitled "Vortex Flow Reducer."

Frame elements 20 and 21 and frame 35 can be made by molding from a suitable plastic material such as polyethylene, polypropylene or the like. As can be seen by reference to FIG. 2, extended portions 27a of struts 27 serve to provide a space between the downstream surface of fibrous layer 13 and the knit tricot sock material on the downstream side of assembly 50. This is advantageous because it provides a "free volume" through which gas originating from defoamed blood can rise upwardly. In addition, this space helps prevent any fiber fragments from reaching the tricot fabric at the downstream end of assembly 50.

In a modification, the blood filtration media 10 may have a layer of knit tricot fabric at its downstream side only. This is accomplished by assembling filtration media sub-unit 30 as described earlier herein. A piece of tricot fabric somewhat larger than the dimension of frame 35 is prepared. Frame 35 is placed on a work surface so that its side walls 38 project upwardly and the prepared piece of tricot fabric is then laid over the side wall edges. Filtration media sub-unit 30 is then snapped into frame 35. The tricot fabric is thereby secured in place between the inner surface of the side walls of frame 35 and the outer surface of the side walls of frame element 21. This modification is more quickly and easily assembled and requires less tricot fabric.

In another modification, a single fibrous layer having a thickness in the range of 0.070 inch (0.178 cm.) to 0.160 inch (0.406 cm.) may be used in place of fibrous layers 11 and 12. Preferably, such a single layer would have a thickness ranging from 0.080 inch (0.203 cm.) to 0.120 inch (0.305 cm.). In such case the fiber denier, pore size, and minimum bubble point are within the ranges recited herein for layers 11 and 12. The weight of such single layer would be in the range of from about 13 ounces per square yard to about 23 ounces per square yard.

While specific embodiments of the invention have been described under the heading "Detailed Description of the Invention," it will be recognized that departures may be made therefrom without departing from the spirit and scope of the invention. Specifically, for example, the fiber denier, fabric pore size and fabric weight of the fibrous layers may be varied as described under the heading "Summary of the Invention." In addition, those skilled in the art will recognize that the various described frame elements may in certain applications be omitted. In these cases, the blood filtration media may simply comprise fibrous layers 11, 12 and 13. Optionally, a layer of tricot fabric may be located on the downstream side of layer 13 or on both the downstream side of layer 13 and the upstream side of layer 11.

What is claimed is:

1. A filtration unit comprising a filtration media sub-unit secured in an outer frame, said filtration media sub-unit comprising a fibrous filtration media enclosed in an inner frame, said inner frame comprising an upstream frame element and a downstream frame element adapted to be matingly engaged with each other with said filtration media being disposed therebetween, each of said frame elements comprising a periphery having a top portion, a bottom portion, and a pair of opposed side portions, each of said frame elements comprising a plurality of longitudinal struts joining its top and bottom portions and a plurality of transverse struts joining its side portions, the intersections of the longitudinal and transverse struts of said frame elements being in a single plane on the side of the frame elements which contacts said filtration media, the longitudinal struts of said downstream frame element having portions which are perpendicular to and project beyond the principal plane of the periphery of said downstream frame element, said outer frame comprising a peripheral member which is L-shaped in cross-section, the horizontal portion of said L-shaped cross-section forming the base of said outer frame and the vertical portion of said L-shaped cross-section forming the side walls of said outer frame, a piece of tricot knit fabric being placed between the downstream frame element of the filtration media sub-unit and said outer frame.

2. A filtration unit comprising a filtration media sub-unit secured in an outer frame, said filtration media sub-unit comprising a fibrous filtration media enclosed in an inner frame, said inner frame comprising an upstream frame element and a downstream frame element adapted to be matingly engaged with each other with said filtration media being disposed therebetween, each of said frame elements comprising a periphery having a top portion, a bottom portion, and a pair of opposed side portions, each of said frame elements comprising a plurality of longitudinal struts joining its top and bottom portions and a plurality of transverse struts joining its side portions, the intersections of the longitudinal and transverse struts of said frame elements being in a single plane on the side of the frame elements which contacts said filtration media, the longitudinal struts of said downstream frame element having portions which are perpendicular to and project beyond the principal plane of the periphery of said downstream frame element, said outer frame comprising a peripheral member which is L-shaped in cross-section, the horizontal portion of said L-shaped cross-section forming the base of said outer frame and the vertical portion of said L- shaped cross-section forming the side walls of said outer frame, said filtration unit being enclosed in a socket of tricot knit fabric.

3. A filtration unit according to claim 1 or 2 in which said portions which are perpendicular to and project beyond the principal plane of the periphery of said downstream frame element are arcuate in configuration.

4. A filtration unit comprising a filtration media sub-unit secured in an outer frame, said filtration media sub-unit comprising a fibrous filtration media enclosed in an inner frame, said inner frame comprising an upstream frame element and a downstream frame element adapted to be matingly engaged with each other with said filtration media being disposed therebetween, each of said frame elements comprising a periphery having a top portion, a bottom portion, and a pair of opposed side portions, each of said frame elements comprising a plurality of longitudinal struts joining its top and bottom portions and a plurality of transverse struts joining its side portions, the intersections of the longitudinal and transverse struts of said frame elements being in a single plane on the side of the frame elements which contacts said filtration media, said outer frame comprising a peripheral member which is L-shaped in cross-section, the horizontal portion of said L-shaped cross-section forming the base of said otuer frame and the vertical portion of said L-shaped cross-section forming the side walls of said outer frame, a piece of tricot knit fabric being placed between the downstream frame element of the filtration media sub-unit and said outer frame.

5. A filtration unit comprising a filtration media sub-unit in an outer frame, said filtration media sub-unit comprising a fibrous filtration media enclosed in an inner frame, said inner frame comprising an upstream frame element and a downsteam frame element adapted to be matingly engaged with each other with said filtration media being disposed therebetween, each of said frame elements comprising a periphery having a top portion, a bottom portion, and a pair of opposed side portions, each of said frame elements comprising a plurality of longitudinal struts joining its top and bottom portions and a plurality of transverse struts joining its side portions, the intersections of the longitudinal and transverse struts of said frame elements being in a single plane on the side of the frame elements which contacts said filtration media, said outer frame comprising a peripheral member which is L-shaped in cross-section, the horizontal portion of said L-shaped cross-section forming the base of said outer frame and the vertical portions of said L-shaped cross-section forming the side walls of said outer frame, said filtration unit being enclosed in a sock of tricot knit fabric.

* * * * *